(12) United States Patent
Chen (10) Patent No.: US 9,033,952 B2
(45) Date of Patent: May 19, 2015

(54) PUNCTURE NEEDLE DEVICE AND METHOD OF USING THE SAME

(71) Applicant: Taipei Veterans General Hospital, Taipei (TW)

(72) Inventor: Pin-Tarng Chen, Taipei (TW)

(73) Assignee: TAIPEI VETERANS GENERAL HOSPITAL, Taipei (TW)

( * ) Notice: Subject to any disclaimer, the term of this patent is extended or adjusted under 35 U.S.C. 154(b) by 0 days.

(21) Appl. No.: 14/034,908

(22) Filed: Sep. 24, 2013

(65) Prior Publication Data

US 2015/0011972 A1     Jan. 8, 2015

(30) Foreign Application Priority Data

Jul. 2, 2013 (TW) .............................. 102123671 A (51) Int. Cl.

| A61M 5/42 | (2006.01) |
|---|---|
| A61B 17/34 | (2006.01) |
| A61M 25/06 | (2006.01) |
| A61B 19/00 | (2006.01) |
| A61B 18/24 | (2006.01) |
| A61M 5/20 | (2006.01) |

(52) U.S. Cl.
CPC ............. *A61M 5/427* (2013.01); *A61B 17/3403* (2013.01); *A61B 2019/202* (2013.01); *A61B 2019/5206* (2013.01); *A61B 18/24* (2013.01); *A61M 25/0631* (2013.01); *A61M 25/0606* (2013.01); *A61M 2005/206* (2013.01); *A61M 5/2033* (2013.01)

(58) Field of Classification Search
CPC . A61M 5/427; A61M 5/3287; A61M 5/2033; A61M 2005/206; A61B 5/15111; A61B 5/15113; A61B 5/15117; A61B 5/1519; A61B 2019/202
USPC ............ 604/116, 156, 157, 158, 130, 164.01, 604/164.12, 249
See application file for complete search history.

(56) References Cited

U.S. PATENT DOCUMENTS

| 4,311,138 A * | 1/1982 | Sugarman ................ 604/165.02 |
| 5,312,361 A * | 5/1994 | Zadini et al. ............. 604/165.02 |
| 2013/0006178 A1* | 1/2013 | Pinho et al. .................. 604/116 |
| 2013/0184680 A1* | 7/2013 | Brewer et al. ................. 604/510 |

* cited by examiner

*Primary Examiner* — Rebecca E Eisenberg
*Assistant Examiner* — Anh Bui
(74) *Attorney, Agent, or Firm* — WPAT, P.C.; Anthony King (57) ABSTRACT

A puncture needle device, comprising a light source assembly, an optic fiber assembly, an ejection assembly, and a puncture needle assembly, wherein the light source assembly comprises a light source sleeve configured with a light source, the optic fiber assembly comprises an optic fiber sleeve configured with an optic fiber, the ejection assembly comprises an ejection sleeve configured with an ejection spring, and the puncture needle assembly comprises a puncture needle with a catheter.

10 Claims, 9 Drawing Sheets

PUNCTURE NEEDLE DEVICE AND METHOD OF USING THE SAME

FIELD OF THE INVENTION

The present invention generally relates to a puncture needle device, in particular a puncture needle device using an optic fiber for locating the puncture site, allowing a needle to puncture along the direction of the optic fiber for precise puncture. In addition, the present invention also discloses a method of using the puncture needle device.

BACKGROUND OF THE INVENTION

For critical or long-term ventilator dependent patients, tracheostomy is always vital to them. Moreover, tracheostomy can help patients to maintain better airway hygiene and to decrease dead space in the breathing tube. As a result, tracheostomy plays an important role in the field of critical or long-term care. In Europe or American area, experts suggest tracheostomy should be early established in patients who cannot maintain their airway or patients who have depended on ventilator more than one week and cannot weaned from ventilator soon (Durbin, Respir Care. 2010 August; 55(8): 1056-68; Mallick et al., Eur J Anaesthesiol. 2010 August; 27(8):676-82; and 2) Dempsey et al., Br J Anaesth. 2010 December; 105(6):782-8).

Traditionally tracheostomy is completed on a patient under general anesthesia in an operation room. Surgeons incise transversely then dissect over the lower neck. After seeing the $2^{nd}$ or $3^{rd}$ trachea ring visibly, they incise the trachea. Then tracheostomy tube is placed into the incision. The patients should be transferred from intensive care units (ICU) or wards to operation rooms. The process of transferring requires the manpower of medical personnel and increases many potential risks. Moreover, many patients are supported with continuous vital drugs such as inotropes or vasopressors, and continuous invasive monitors are necessary for them. The transferring risk and difficulty may largely increase in such situation.

The general procedures of "percutaneous dilatational tracheostomy (PDT)" are described as below. After surface locating the surgical area, the surgeon incises 1.5 to 2 cm wound. Then the bronchoscope is inserted into the patient's previous placed endotracheal tube. When the bronchoscope is placed over the tip of endotracheal tube, the endotracheal tube and bronchoscope will be withdrawn slowly. After the light of bronchoscope pass the incision wound, the surgeon will see the light emitted from bronchoscope over the incision area. Subsequently, under bronchoscope examination and guidance, the surgeon tries to locate and puncture. When the puncture advances the trachea, guiding wire is placed. Later, the special dilatational instruments are used in turn for dilating subcutaneous tissue and anterior trachea wall.

In Taipei Veterans General Hospital, we have developed percutaneous dilatational tracheostomy (PDT) for more than a decade. At present we complete most PDT at bedside in the intensive care units. When the patients are under intravenous general anesthesia, both anesthesiologists and chest surgeons cooperate to do this invasive operation. Anesthesiologists are responsible for bronchoscope examination and guidance. On the other hand, chest surgeons are responsible for puncture and tracheostomy creation. In our medical center, about one third tracheostomy operations were done by this at bedside PDT technique. Through this method we can decrease the transferring risks and enhance patient safety. Further, we can make the medical resource application and operation room usage more efficiently.

In our experience, the most critical and danger step of PDT is how to proper puncture the needle into trachea. Traditionally we use instrument lightly compress trachea wall then we can locate the puncture site according to the change due to trachea compression under bronchoscopy. If there is any deviation of puncture, this may cause damage to the neighboring tissue such as thyroid gland or blood vessels. In addition, if the puncture angle or direction is not good, that may lead to the difficulty of the guiding wire placement or impossibility to observe the process of puncture under bronchoscopy. Moreover, it may lead to the puncture to bronchoscope then cause the damage to bronchoscope. All above conditions will prolong surgical time, or increase the puncture times, or cause the endotracheal tube dislodgement. The chance of such difficult operation or complications is related to the patient's airway anatomy, duration of endotracheal tube placement, skill and experience of the operator, and communication between the bronchoscope examiner and the operator. In a word, the traditional method tends to cause the above-mentioned complications. Accordingly, the present invention is to provide a device and a method for more accurate and safer guidance, locating, and puncture.

SUMMARY OF THE INVENTION

In one aspect, the present invention provides a puncture needle device, comprising a light source assembly, an optic fiber assembly, an ejection assembly, and a puncture needle assembly, wherein the light source assembly comprises a light source sleeve configured with a light source, the optic fiber assembly comprises an optic fiber sleeve configured with an optic fiber, the ejection assembly comprises an ejection sleeve configured with an ejection spring, and the puncture needle assembly comprises a puncture needle with a catheter.

According to one embodiment of the present invention, the light source assembly, the optic fiber assembly, the ejection assembly, and a puncture needle assembly may have the following structures.

The light source assembly comprises a switch unit, a light source sleeve, and an adaptor unit, a rear end of the switch unit being coupled to a front end of the light source sleeve, and the adaptor unit being coupled to a rear end of the light source sleeve. In addition, a front end of the switch unit is configured with a switch; a battery is positioned within the light source sleeve; the adaptor unit is configured with a LED module and a battery contact spring.

The optic fiber assembly comprises an optic fiber sleeve; a stopper positioned within the optic fiber sleeve at a front end of the optic fiber sleeve; and an optic fiber positioned axially within the optic fiber sleeve, with a front end thereof fixed to the stopper and a rear end thereof extending into and protruding slightly out of the puncture needle assembly. In addition, a front end of the optic fiber sleeve may be coupled to a rear end of the adaptor unit of the light source assembly, allowing the light source assembly and the optic fiber assembly to combine to form a single element.

According to said embodiment of the present invention, the ejection assembly comprises an ejection sleeve, an ejection spring, and an ejection button module, wherein a rear end of the ejection sleeve is configured with a puncture needle adaptor unit, the ejection sleeve is slidable within the optic fiber sleeve, and the ejection spring is positioned within the ejection sleeve. In addition, the ejection button module, in coordination with the optic fiber sleeve, allows the ejection sleeve to stay still within the optic fiber sleeve, and upon triggering allows the ejection spring to release and eject the ejection sleeve. The ejection assembly allows ejection of the puncture needle for automatic puncture.

The puncture needle assembly comprises an over-the-needle catheter, a puncture needle, and a connector for coupling to the puncture needle adaptor unit of the ejection assembly. In the present embodiment, the puncture needle assembly is just a traditional intravenous catheter as used clinically.

In one specific embodiment, the ejection button module comprises: at least one ejection button, and at least one positioning hole configured at the surrounding of the ejection sleeve. In addition, at least one positioning groove is coordinately configured at the optic fiber sleeve, which may be generally in the shape of "L" and have a longitudinal guiding section and a horizontal positioning section. Wherein, the at least one ejection button may pass through the positioning groove and fixed to the at least one positioning hole, and the sliding distance of the ejection sleeve is constrained by the guiding section on the optic fiber sleeve.

According to the present invention and as described above, the light source assembly and the optic fiber assembly may combine to form a single element, and the ejection assembly and the puncture needle assembly may combine to form a single element, allowing the ejection assembly be slidably connected to the optic fiber assembly, and the optic fiber of the optic fiber assembly pass through the ejection assembly and protrude slightly out of the puncture needle of the puncture needle assembly, thereby the light from the light source may travel along the optic fiber and project on the intending puncture area in front of the puncture needle for locating a proper puncture site, and the puncture needle assembly may be ejected and punctured into the proper puncture site by the ejection assembly.

In another aspect, the present invention provides a method of using the puncture needle device, comprising the following steps: (A) determining an intending puncture area on an organ with a lumen or cavity; (B) activating the light source of the light source assembly; (C) observing at least one projection of the light on the organ and adjusting the orientation of the puncture needle device to aiming at a proper puncture site according to the shape of the at least one projection; (D) launching the ejection sleeve the ejection assembly to allow the puncture needle assembly to puncture into the lumen or cavity of the organ; and (E) leaving the catheter and removing the puncture needle and the optic fiber along with the rest of the puncture needle device.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

In one aspect, the present invention provides a puncture needle device, comprising a light source assembly, an optic fiber assembly, an ejection assembly, and a puncture needle assembly, wherein the light source assembly comprises a light source sleeve configured with a light source, the optic fiber assembly comprises an optic fiber sleeve configured with an optic fiber, the ejection assembly comprises an ejection sleeve configured with an ejection spring, and the puncture needle assembly comprises a puncture needle with a catheter.

Certain preferred embodiments of the present invention are described below.

Figure 1:
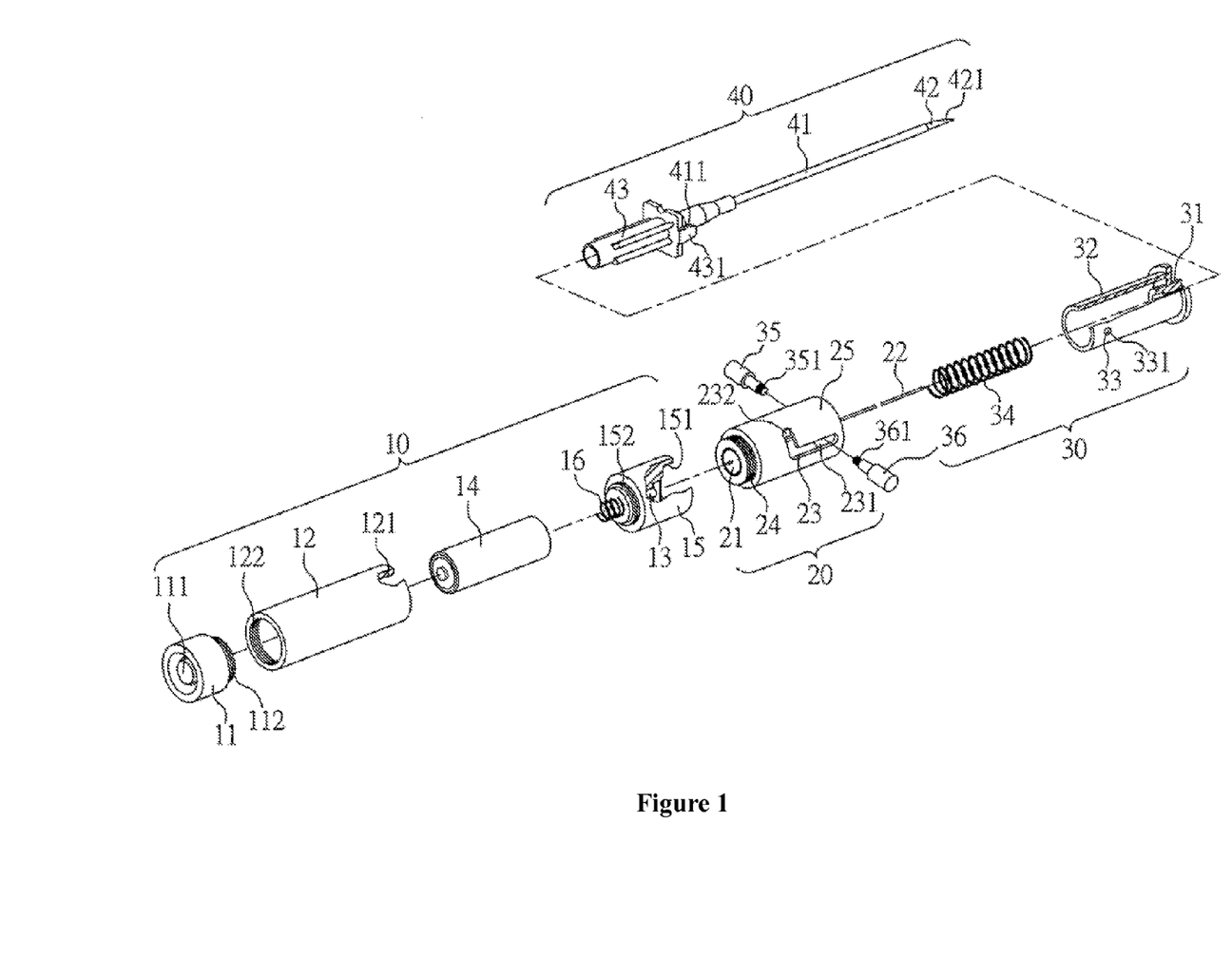
FIG. 1 is an exploded view of the puncture needle device according to one embodiment of the present invention.
Figure 2:
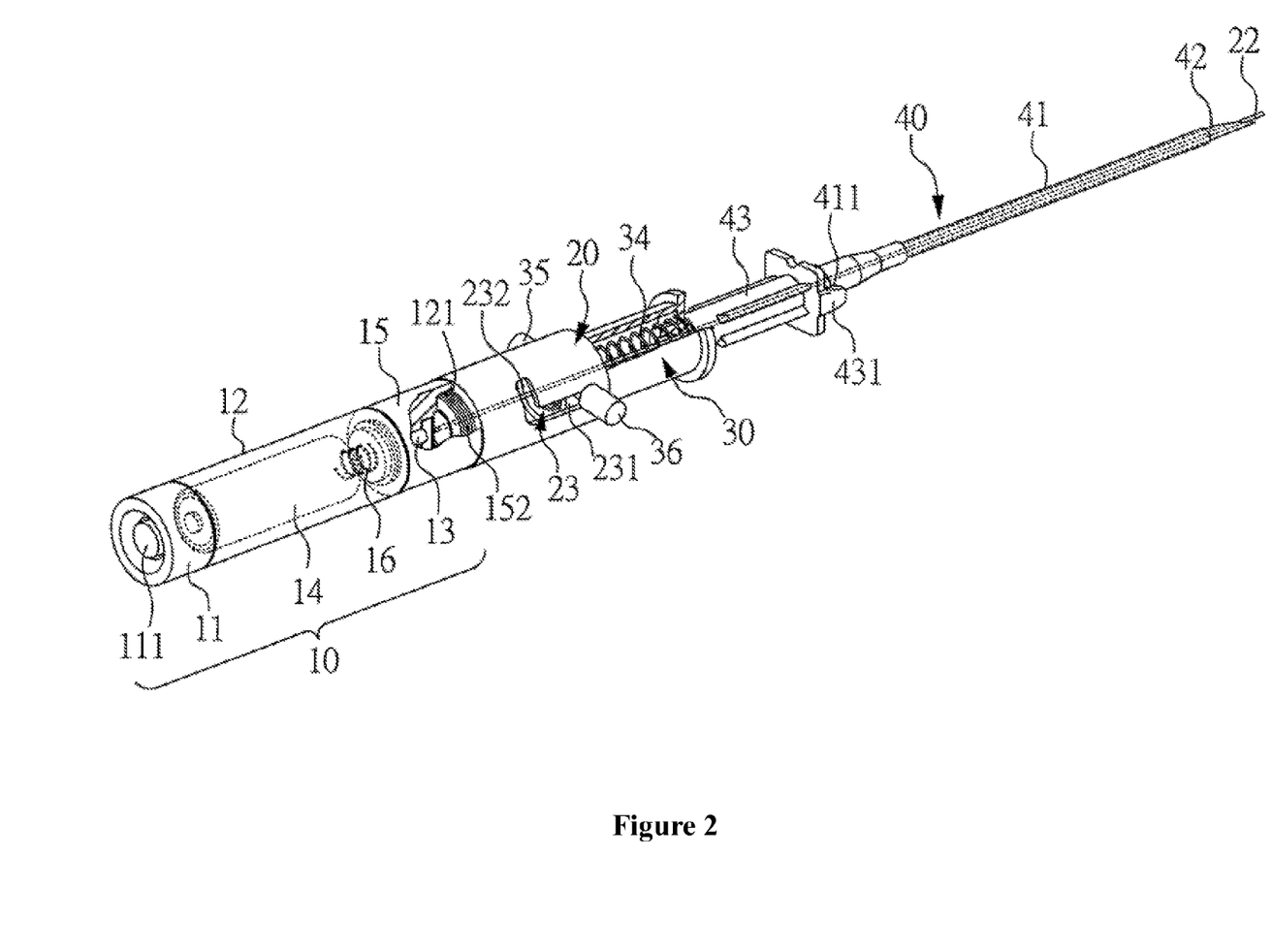
FIG. 2 is a perspective view of the puncture needle device according to one embodiment of the present invention.
Figure 3:
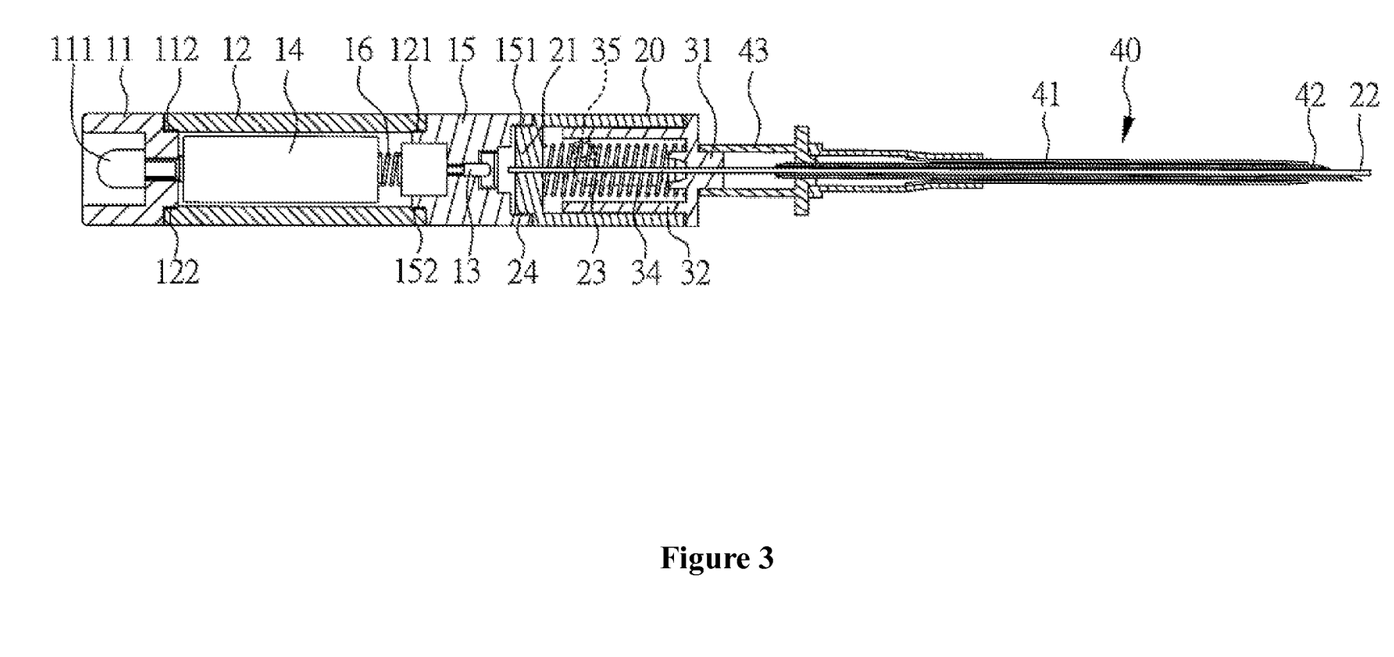
FIG. 3 is a sectional view of the puncture needle device according to one embodiment of the present invention.

With reference to FIGS. 1-3, provided is a puncture needle device, comprising a light source assembly 10, an optic fiber assembly 20, an ejection assembly 30, and a puncture needle assembly 40, wherein the light source assembly 10 comprises a cylindrical switch unit 11, a cylindrical light source sleeve 12, and a cylindrical adaptor unit 15, all having the same cylindrical outer diameter, and the switch unit 11 being coupled to a front end of the light source sleeve 12 through an external thread 112 at a rear end of the switch unit 11 and an internal thread 122 at the front end of the light source sleeve 12; the adaptor unit 15 is coupled to a rear end of the light source sleeve 12 through an internal thread 121 at the rear end of the light source sleeve 12 and an external thread 152 at a front end of the adaptor unit 15; a switch button 111 is configured at a front end of the switch unit 11, allowing turning on or off the power by pressing; a battery 14 (e.g. a lithium battery) is placed in the light source sleeve 12; and a LED module 13 is configured at/within the adaptor unit 15, with the end neighboring to the battery 14 configured with a battery contact spring 16, allowing the battery 14 to be in position within the light source sleeve 12 and form a current loop, and the other end of the LED module 13 to emit a light beam.

According the present invention, the light beam emitted from the LED module 13 is preferably at an energy level sufficient to penetrate an anterior wall of a hollow organ tissue (e.g. the anterior wall of trachea), while at the same time not causing any tissue injury during operation. On the other hand, the light source assembly is preferably designed according to electric machinery and electromagnetic safety standard so that it would not cause any accident during operation. In certain embodiments, the light source assembly or the puncture needle device is designed to be light and portable.

The optic fiber assembly 20 comprises a optic fiber sleeve 25; a stopper 21 positioned and fixed within the optic fiber sleeve 25 at a front end thereof; and an optic fiber 22 positioned axially within the optic fiber sleeve 25, with a front end thereof fixed to the stopper 21 and a rear end thereof extending into and protruding slightly out of the puncture needle of the puncture needle assembly 40.

According the present invention, the outer diameter of the optic fiber 22 is preferably that allows it to pass through the puncture needle (the puncture needle used in the present invention is generally a 16-18 Ga. needle) smoothly, and allows transmission of the required light source. In addition, the optic fiber 22 is preferably having a certain extent of rigidity to decrease the possible twist or torsion during the process of "aiming then puncture," and is preferably allowing disinfection or being disposable.

An external thread 24 is configured at a front end of the optic fiber sleeve 25 for coupling to an internal thread 151 at a rear end of the adaptor unit 15 of the light source assembly 10, allowing the light source assembly 10 and the optic fiber assembly 20 to combine to form a single element through the threads. Further, two positioning groove 23 are configured at symmetric positions on the optic fiber sleeve, each being generally in the shape of "L" and having a longitudinal guiding section 231 and a horizontal positioning section 232.

The ejection assembly 30 comprises an ejection sleeve 32, an ejection spring 34, and two ejection button modules each including an ejection button (ejection button 35 or 36) and a positioning hole 33, wherein a rear end of the ejection sleeve 32 is configured with a puncture needle adaptor unit 31, and the two positioning holes 33 is configured at symmetric positions at the surrounding of the ejection sleeve 32 with each positioning hole configured with internal thread 331 within. The ejection assembly 30 is installed to the optic fiber sleeve 25 in a manner such that it is slidable within but do not break away from the optic fiber sleeve 25: first the ejection spring 34 is installed into the ejection sleeve 32, and then the ejection sleeve 32 is placed into the optic fiber sleeve 25 to allow the two positioning holes 33 of the ejection sleeve 32 to align with the two L-shaped longitudinal guiding sections 231 of the optic fiber sleeve 25, respectively; and respectively locks the ejection buttons 35 and 36 into the two positioning holes 33 of the ejection sleeve, through external threads 351, 361 and the internal threads 331.

The ejection assembly 30 allows automatic puncture through releasing the ejection spring 34 by the ejection button 35 or 36. Due to different hand-hold stabilities of the users, it is possible that in the process of puncture the actual puncture site is deviated from the proper puncture site as located through optic positioning. Thus, this ejection device is designed for automatic puncture through the ejection button 35 or 36, to reduce the error caused by hand-hold stability of the users.

The puncture needle assembly 40 comprises a plastic intravenous catheter 41, a steel puncture needle 42, and a connector 43, wherein the connector 43 is socketed to the puncture needle adaptor 31 of the ejection assembly 30 through a rear end thereof; the puncture needle 42 is fixed to the connector 43 at its front end; and the puncture needle 42 is nested in the intravenous catheter 41 with a flange 411 of the intravenous catheter 41 clamped to a locking portion 431 of the connector 43 and the needle tip 421 of the puncture needle 42 protruding slightly out of the intravenous catheter 41. Thus, the ejection assembly 30 and the puncture needle assembly 40 may be combined to form a single element. According to the present invention, the puncture needle assembly may be commercially available.

According to the present invention, in operation, as shown in FIGS. 4, 5, 5a, 6 and 6a, the ejection sleeve 32 is slidable within the optic fiber sleeve 25, and the two ejection buttons 35 and 36 locked into the two positioning holes 33 of the ejection sleeve 32 are slidable along the longitudinal guiding sections 231 of the optic fiber sleeve 25. As shown in FIGS. 2, 3, 6, and 6a, the ejection buttons 35 and 36 are at the terminals of the guiding sections 231, indicating that the ejection spring 34 is in a release status; and if the ejection buttons 35 and 36 are at the positioning sections 232, the ejection spring 34 is in a compressed status (see FIGS. 5 and 5a).

Figure 4:
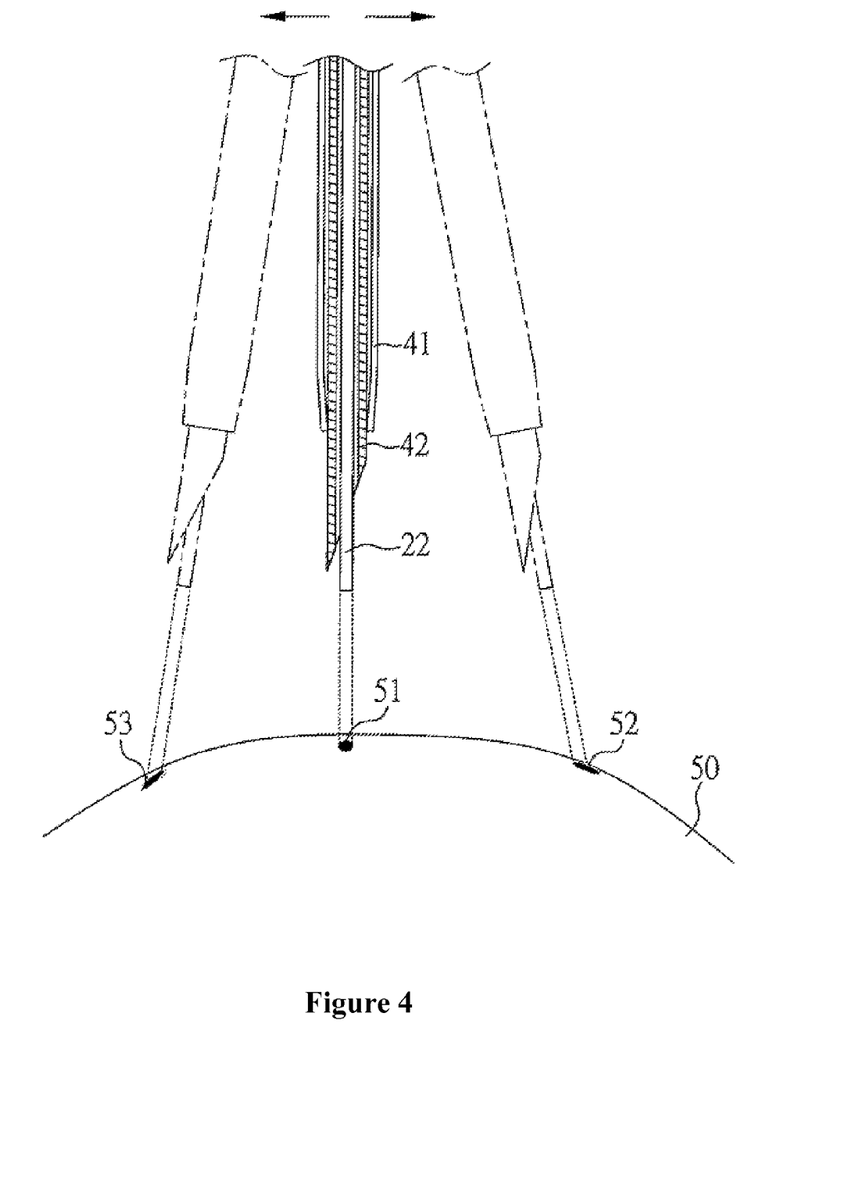
FIG. 4 illustrates the step of observing at least one projection of the light on the organ and adjusting the orientation of a puncture needle device to aim at a proper puncture site, according to one embodiment of the present invention.

As illustrated in FIG. 4, the light beam from the optic fiber 22 should be projected at a proper puncture site 51 on an intending puncture area 50 before starting the puncture. In the aiming process, if the light beam from the optic fiber 22 is aimed and projected at an improper puncture site 52 or 53, its projection presents a diffused elliptical shape, rather than a focused circular shape when it is projected at the proper puncture site 51.

Figure 5:
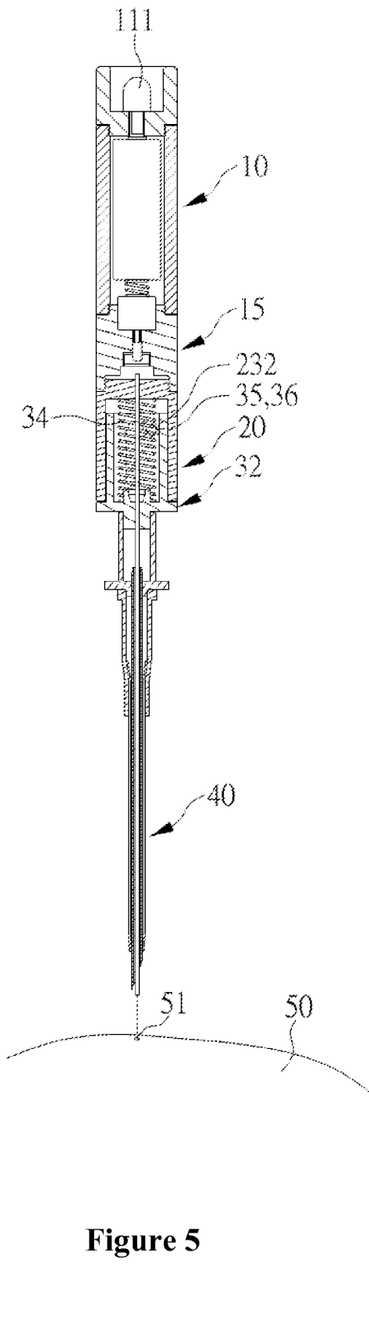
FIG. 5 is a schematic view of a puncture needle device which has aimed at a proper puncture site before launching the ejection sleeve of the ejection assembly, according to one embodiment of the present invention.
Figure 5A:
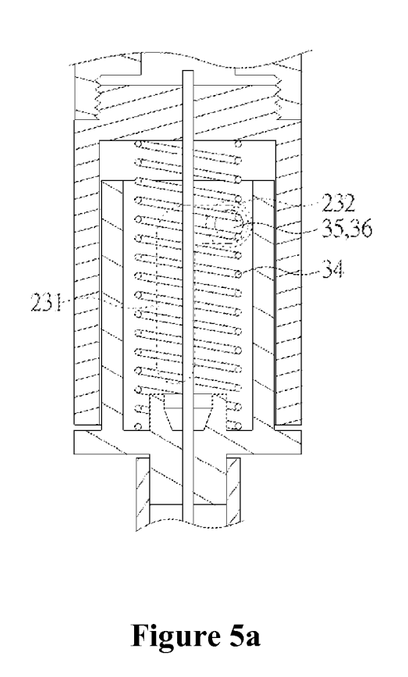
FIG. 5a is a partially enlarged view of FIG. 5, showing that before launching the ejection sleeve of the ejection assembly, the ejection spring of the ejection assembly is in a compressed status and the at least one ejection button is at the location of the positioning section of the optic fiber sleeve.
Figures 6, 6A:
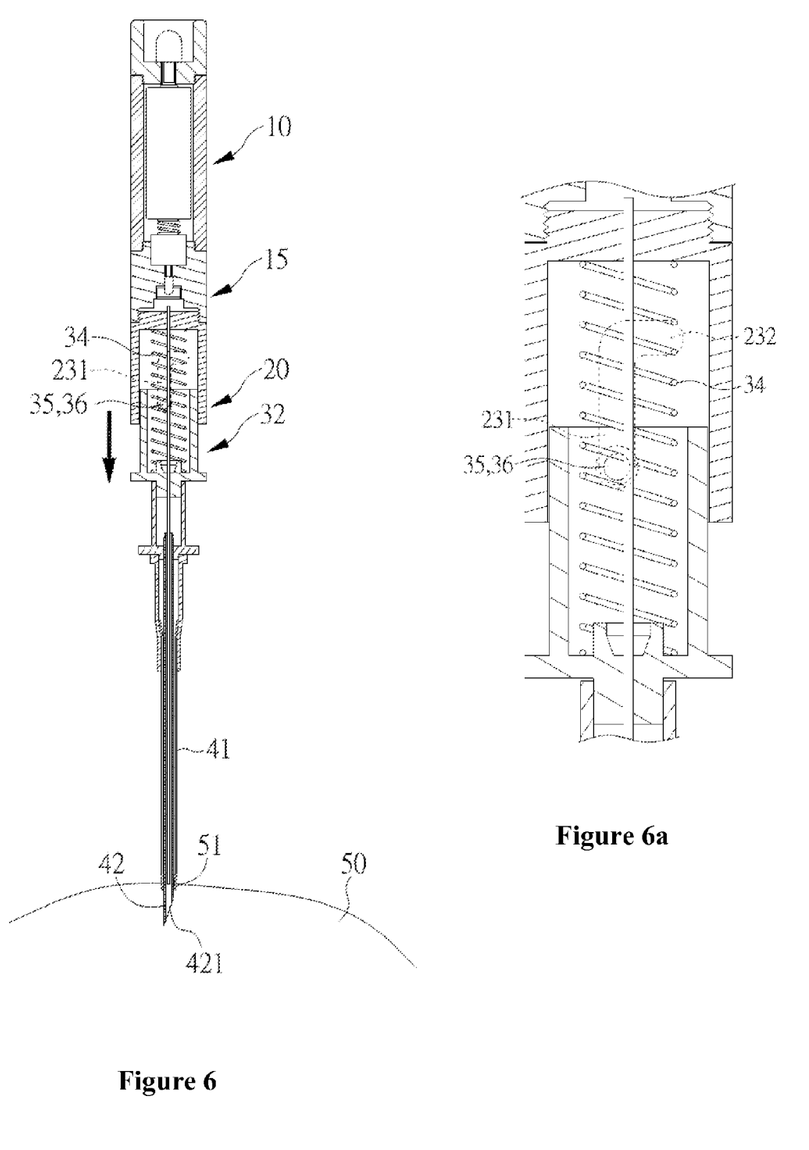
FIG. 6 illustrates the step of launching the ejection sleeve the ejection assembly to allow a puncture needle assembly to puncture into the lumen or cavity of an organ, according to one embodiment of the present invention.
FIG. 6a is a partially enlarged view of FIG. 6, showing that after launching the ejection sleeve of the ejection assembly, the ejection spring of the ejection assembly is in a release status and the at least one ejection button is at the location of the guiding section of the optic fiber sleeve.
Figure 7:
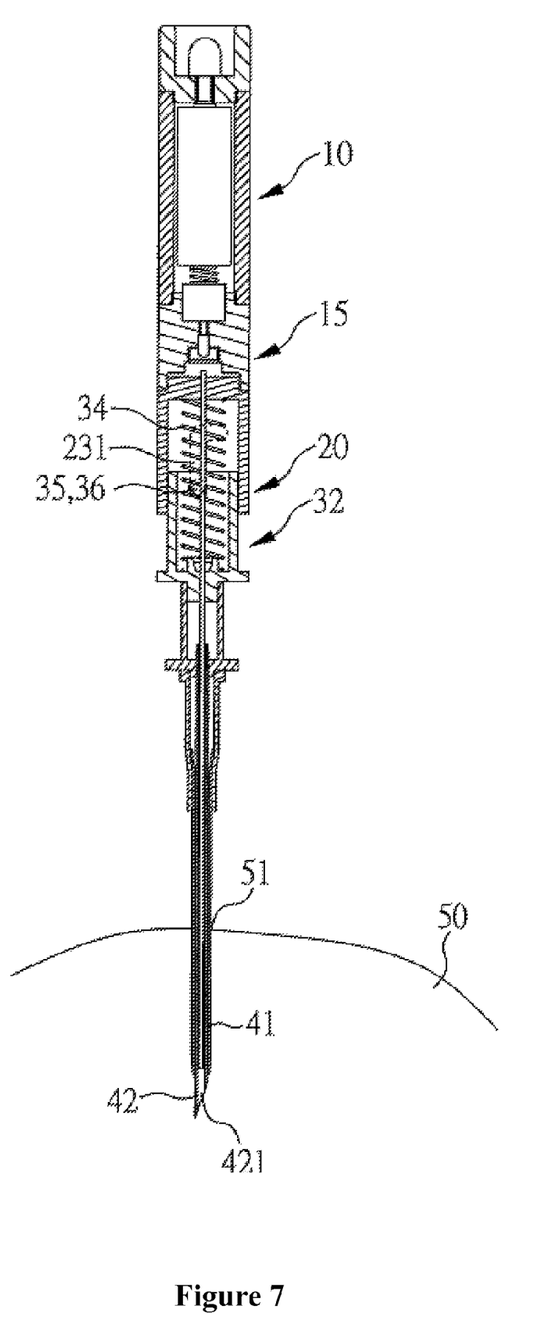
FIG. 7 is a schematic diagram showing that a puncture needle assembly of a puncture needle device punctures into a lumen or cavity of an organ, according to one embodiment of the present invention.
Figure 8:
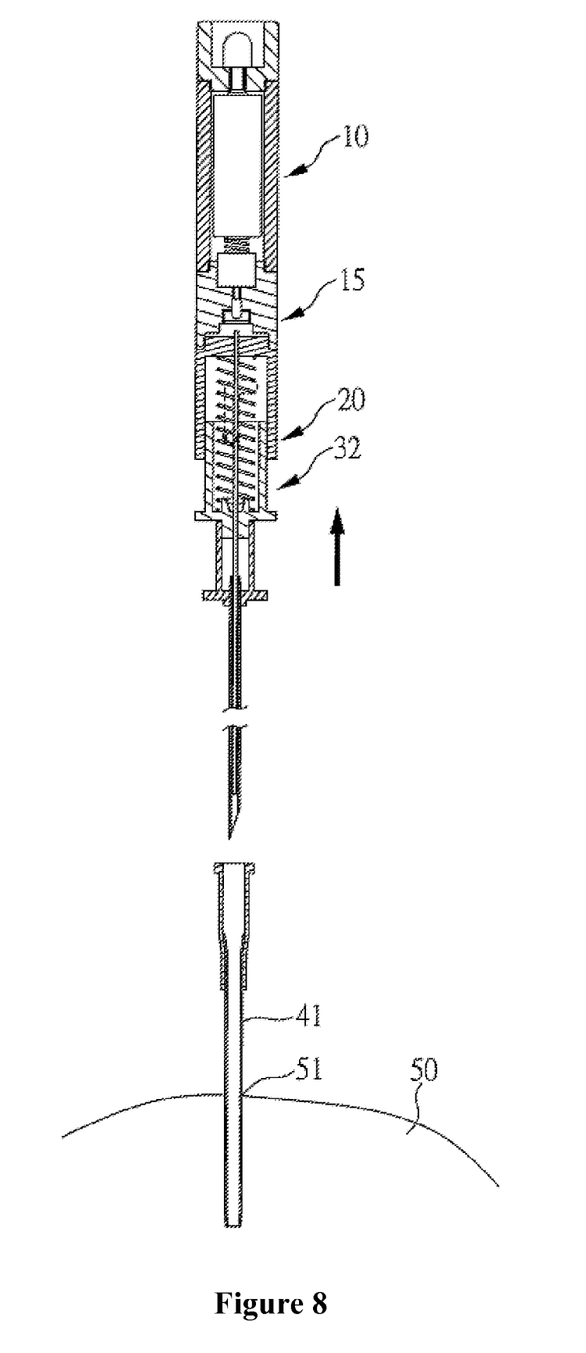
FIG. 8 illustrates the step of leaving the catheter and removing the puncture needle and the optic fiber along with the rest of the puncture needle device, according to one embodiment of the present invention.

When the ejection button 35 or 36 is pushed from the positioning section 232 to slide to the terminal of the guiding section 231, the puncture needle assembly transforms from its pre-ejected status as shown in FIGS. 5 and 5a to its post-ejected status as shown in FIGS. 6 and 6a.

In another aspect, the present invention provides a method of using the puncture needle device, comprising the following steps: (A) determining an intending puncture area on an organ with a lumen or cavity; (B) activating the light source of the light source assembly; (C) observing at least one projection of the light on the intending puncture area and adjusting the orientation of the puncture needle device to aim at a proper puncture site according to the shape of the at least one projection; (D) launching the ejection sleeve of the ejection assembly to allow the puncture needle assembly to puncture into the lumen or cavity of the organ; and (E) leaving the catheter and removing the puncture needle and the optic fiber along with the rest of the puncture needle device.

Figure 9:
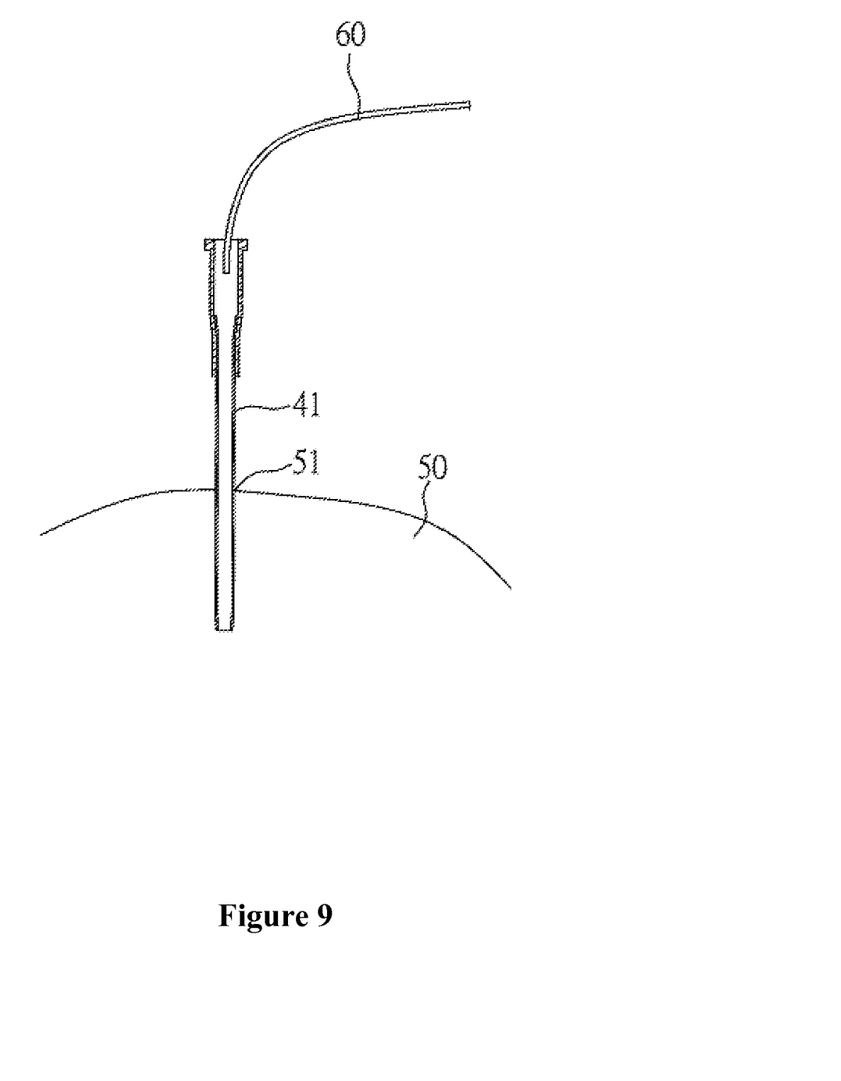
FIG. 9 illustrates how a guiding wire is introduced into a lumen or cavity of an organ via the catheter.

In one embodiment, the method of using the puncture needle device comprises the following steps: (A-0) incising a wound over a skin of a subject and extending the wound subcutaneously to expose an organ with a lumen or cavity; (A) determining an intending puncture area 50 on the organ; (B) activating the light source through the switch button 111 of the light source assembly 10; (C) observing at least one projection of the light on the intending puncture area 50 and adjusting the orientation of the puncture needle device to aim at a proper puncture site 51 according to the shape of the at least one projection; (D) launching the ejection sleeve 32 of the ejection assembly 30 to allow the puncture needle assembly 40 to puncture into the lumen or cavity of the organ; (E) leaving the intravenous catheter 41 and removing the puncture needle 42 and the optic fiber 22 along with the rest of the puncture needle device; (F) introducing through the intravenous catheter 41 a guiding wire 60 into the lumen or cavity of the organ (see FIG. 9).

EXAMPLES

Example 1

Animal (Swine) Study

When the swine is under intravenous general anesthesia, a disposable laryngeal mask airway (LMA) is placed over its larynx. After anesthesia, we placed the swine in supine position and extended its neck. Through ultrasound localization and palpation, the thyroid cartilage, cricoid cartilage, and trachea ring was localized and proper site for operation was chosen. Subsequently, incised 2 cm wound over the skin of the lower neck and extended this incision wound subcutaneously. A wireless endoscope was introduced into the trachea via LMA with its tip located at $1^{st}$ or $2^{nd}$ trachea ring cartilage. Then the puncture needle device of the present invention was placed over the intending puncture site on the trachea wall and the light source was activated. The light spot projecting on the posterior tracheal wall under endoscopy can be observed through the endoscope. To ensure the puncture is in the middle of the trachea, we made the light spot locate at the midline of the trachea. If there is any deviation of localization, the endoscopy examiner should feedback to the surgeon timely. After adjusting the optic fiber to be in the midline of the trachea according to light spot guidance, the localization was completed. Then we observed the traveling direction of the light. The proper direction should be vertical to the midline of the anterior trachea wall. The endoscopy examiner and surgeon communicated with each other and adjust the orientation of the puncture needle device and the optic fiber by the light spot change under endoscopy. Subsequently, under the optic fiber guidance the puncture needle was punctured into the anterior tracheal wall over the optic fiber. The catheter was pushed into the trachea lumen, and we left the catheter in the trachea and remove the optic fiber and puncture needle. Then a guiding wire was introduced into the trachea lumen via the catheter.

Example 2

Human Case

The patient is to be under general anesthesia (intravenous anesthesia and muscle relaxant are used) in ICU. We will suck the endotracheal tube and oral cavity to decrease the secretion. After anesthesia we let the patient in supine position with their neck extended. After palpating the thyroid cartilage, cricoid cartilage, and trachea ring cartilage, we confirm the location by ultrasound. Then a proper intending puncture site (about the space between 2nd and 3rd trachea ring) is chosen. Subsequently, incise 2 cm wound over the skin of the lower neck and properly extended this incision wound subcutaneously. A bronchoscope is placed into the previously placed endotracheal tube and let the scope tip over the endotracheal tube tip. At the same time we slowly withdraw the endotracheal tube and bronchoscope. When the bronchoscope tip passes the incision wound (bronchoscope tip usually is below the cricoid cartilage or between $1^{st}$ or $2^{nd}$ tracheal ring), we start to observe the optic-fiber projecting light spot over the posterior wall of trachea under bronchoscopy. To ensure the puncture is in the middle of the trachea, we make the light spot locate at the midline of the trachea. If there is any deviation of localization, the endoscopy examiner should feedback to the surgeon timely. After adjusting the optic fiber to be in the midline of trachea according to light spot guidance, the localization is completed. Then we observe the traveling direction of the light. The proper direction of light source should be vertical to the midline of anterior trachea wall. The endoscopy examiner and surgeon communicated with each other and adjust the orientation of the puncture needle device and the optic fiber by the light spot change under bronchoscopy. Subsequently, under the optic fiber guidance the puncture needle is punctured into the anterior tracheal wall over the optic fiber. The catheter was pushed into the trachea lumen, and we left the catheter in the trachea and remove the optic fiber and puncture needle. Then a guiding wire was introduced into the trachea lumen via the catheter. The surgeon uses the attached dilators in sequence to dilate the subcutaneous tissue and anterior tracheal wall. Under the monitor of bronchoscopy, the tracheostomy tube placement is completed. Use bronchoscope to suck the tracheostomy tube. Subsequently, fix the tracheostomy tube then put the patient to neutral position.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

I claim:

1. A puncture needle device comprising a light source assembly, an optic fiber assembly, an ejection assembly, and a puncture needle assembly, wherein the light source assembly comprises a light source sleeve configured with a light source; the optic fiber assembly comprises an optic fiber sleeve configured with an optic fiber; the ejection assembly comprises an ejection sleeve configured with an ejection spring and being slidably positioned within the optic fiber sleeve; the puncture needle assembly comprises a puncture needle with a catheter and is coupled to the ejection sleeve; and the ejection spring is positioned within the ejection sleeve and is adapted to eject the ejection sleeve out of the optic fiber sleeve upon release.

2. A puncture needle device comprising:
a light source assembly comprising a switch unit, a light source sleeve, and an adaptor unit;
an optic fiber assembly comprising an optic fiber sleeve, a stopper positioned within the optic fiber sleeve, and an optic fiber positioned axially within the optic fiber sleeve;
an ejection assembly comprising an ejection sleeve, an ejection spring, and ejection button module, wherein a rear end of the ejection sleeve is configured with a puncture needle adaptor unit, the ejection sleeve is slidable within the optic fiber sleeve, and the ejection spring is positioned within the ejection sleeve and is adapted to eject the ejection sleeve out of the optic fiber sleeve upon release; and
a puncture needle assembly comprising an over-the-needle catheter, a puncture needle, and a connector, the puncture needle assembly being coupled to the puncture needle adaptor unit of the ejection sleeve through the connector.

3. The puncture needle device of claim 2, wherein the ejection button module comprises at least one ejection button, and at least one positioning hole configured at the surrounding of the ejection sleeve.

4. The puncture needle device of claim 3, wherein the light source sleeve is configured with at least one positioning groove in the shape of "L" and have a longitudinal guiding section and a horizontal positioning section; and the at least one ejection button passes through the at least one positioning groove and fixed to the at least one positioning hole.

5. The puncture needle device of claim 2, wherein a rear end of the switch unit is coupled to a front end of the light source sleeve, and the adaptor unit is coupled to a rear end of the light source sleeve.

6. The puncture needle device of claim 2, wherein a front end of the switch unit is configured with a switch; a battery is positioned within the light source sleeve; the adaptor unit is configured with a LED module and a battery contact spring.

7. The puncture needle device of claim 2, wherein the stopper is positioned within the optic fiber sleeve at an front end of the optic fiber sleeve; and the optic fiber is positioned axially within the optic fiber sleeve, with an front end thereof fixed to the stopper and an rear end thereof extending into and protruding slightly out of the puncture needle assembly.

8. A method of using the puncture needle device of claim 1, comprising the following steps: (A) determining an intending puncture area on an organ with a lumen or cavity; (B) activating the light source of the light source assembly; (C) observing at least one projection of the light on the organ and adjusting the orientation of the puncture needle device to aiming at a proper puncture site according to the shape of the at least one projection; (D) launching the ejection sleeve the ejection assembly to allow the puncture needle assembly to puncture into the lumen or cavity of the organ; and (E) leaving the catheter and removing the puncture needle and the optic fiber along with the rest of the puncture needle device.

9. The puncture needle device of claim 1, wherein the ejection assembly further comprises at least one ejection button, and at least one positioning hole configured at the surrounding of the ejection sleeve.

10. The puncture needle device of claim 9, wherein the light source sleeve is configured with at least one positioning groove in the shape of "L" and have a longitudinal guiding section and a horizontal positioning section; and the at least one ejection button passes through the at least one positioning groove and fixed to the at least one positioning hole.

\* \* \* \* \*